US008200327B2

(12) United States Patent
Southam et al.

(10) Patent No.: US 8,200,327 B2
(45) Date of Patent: *Jun. 12, 2012

(54) DEVICE FOR TRANSDERMAL ELECTROTRANSPORT DELIVERY OF FENTANYL AND SUFENTANIL

(75) Inventors: Mary Southam, Menlo Park, CA (US); Keith J. Bernstein, Somerville, NJ (US); Henk Noorduin, Bergen op Zoom (NL)

(73) Assignee: ALZA Corporation, Vacaville, CA (US)

( * ) Notice: Subject to any disclaimer, the term of this patent is extended or adjusted under 35 U.S.C. 154(b) by 1261 days.

This patent is subject to a terminal disclaimer.

(21) Appl. No.: 11/456,952

(22) Filed: Jul. 12, 2006

(65) Prior Publication Data
US 2006/0275352 A1 Dec. 7, 2006

Related U.S. Application Data

(63) Continuation of application No. 11/260,976, filed on Oct. 28, 2005, now Pat. No. 7,302,293, which is a continuation of application No. 10/190,022, filed on Jul. 2, 2002, now Pat. No. 7,018,370, which is a continuation of application No. 09/781,041, filed on Feb. 9, 2001, now Pat. No. 6,425,892, which is a continuation of application No. 08/952,657, filed as application No. PCT/US96/07380 on May 22, 1996, now Pat. No. 6,216,033, which is a continuation-in-part of application No. 08/460,785, filed on Jun. 5, 1995, now abandoned.

(51) Int. Cl.
*A61N 1/30* (2006.01)

(52) U.S. Cl. .......................................... 604/20; 604/501

(58) Field of Classification Search .............. 604/19–21, 604/501; 607/115, 148; 424/448–449
See application file for complete search history.

(56) References Cited

U.S. PATENT DOCUMENTS

| 4,141,359 A | 2/1979 | Jacobsen et al. |
| 4,474,570 A | 10/1984 | Ariura et al. |
| 4,588,580 A | 5/1986 | Gale et al. |
| 4,752,285 A | 6/1988 | Petelenz et al. |
| 4,822,802 A | 4/1989 | Levy et al. |
| 4,878,892 A | 11/1989 | Sibalis et al. |
| 4,931,046 A | 6/1990 | Newman |

(Continued)

FOREIGN PATENT DOCUMENTS

GB   2239803   7/1991

(Continued)

OTHER PUBLICATIONS

Gourlay, Geoffrey K., "The Transdermal Administration of Fentanyl in the Treatment of Postoperative Pain: Pharmacokinetics and Pharmacodynamic Efects", *Pain*, 37 (1989), Elsevier Science Publishers B.V. (Biomedical Division), 193-202.

(Continued)

*Primary Examiner* — Quynh-Nhu H Vu
(74) *Attorney, Agent, or Firm* — Shay Glenn LLP

(57) ABSTRACT

The invention provides an improved electrotransport drug delivery system for analgesic drugs, namely fentanyl and sufentanil. The fentanyl/sufentanil is provided as a water soluble salt (e.g., fentanyl hydrochloride), preferably in a hydrogel formulation, for use in an electrotransport device. In accordance with the present invention, a transdermal electrotransport delivered dose of fentanyl/sufentanil is provided which is sufficient to induce analgesia in (e.g., adult) human patients suffering from moderate-to-severe pain associated with major surgical procedures.

6 Claims, 3 Drawing Sheets

U.S. PATENT DOCUMENTS

| | | | |
|---|---|---|---|
| 5,006,108 A | 4/1991 | LaPrade | |
| 5,019,034 A | 5/1991 | Weaver et al. | |
| 5,047,007 A | 9/1991 | McNichols et al. | |
| 5,135,477 A | 8/1992 | Untereker et al. | |
| 5,135,479 A | 8/1992 | Sibalis et al. | |
| 5,203,768 A * | 4/1993 | Haak et al. | 604/20 |
| 5,224,927 A | 7/1993 | Tapper | |
| 5,224,928 A | 7/1993 | Sibalis et al. | |
| 5,232,438 A | 8/1993 | Theeuwes et al. | |
| 5,232,448 A | 8/1993 | Zdeb | |
| 5,246,418 A | 9/1993 | Haynes et al. | |
| 5,254,081 A | 10/1993 | Maurer et al. | |
| 5,320,597 A | 6/1994 | Sage, Jr. et al. | |
| 5,358,483 A | 10/1994 | Sibalis | |
| 6,171,294 B1 * | 1/2001 | Southam et al. | 604/501 |
| 6,216,033 B1 * | 4/2001 | Southam et al. | 604/20 |
| 6,425,892 B2 * | 7/2002 | Southam et al. | 604/501 |
| 7,018,370 B2 * | 3/2006 | Southam et al. | 604/501 |
| 7,302,293 B2 * | 11/2007 | Southam et al. | 604/20 |

FOREIGN PATENT DOCUMENTS

| | | |
|---|---|---|
| JP | 6509254 | 10/1994 |
| JP | 7067971 | 3/1995 |
| JP | 7124265 | 5/1995 |
| WO | WO90/03825 | 4/1990 |
| WO | WO93/01807 | 2/1993 |
| WO | PCT/US95/04497 | 10/1995 |
| WO | WO95/27530 | 10/1995 |
| WO | WO96/39222 | 12/1996 |

OTHER PUBLICATIONS

Hewson, G, et al., "The Effects of Anilldopiperidine Analgesics on Single Respiratory and Non-respiratory Neurones in the Brain Stem of the Rat", *Life Sci.* 31 (20-21), (Nov. 1982), 2335-2338.

Preat, Veronique, "Transdermal Iontophoretic Delivery of Sufentanil", *Elsevier Science Publishers B.V.*, International Journal of Pharmaceutics, 96, (1993), 189-196.

Sebel, P. S., "Transdermal Absorption of Fentanyl and Sufentanil in Man", *European Journal of Clinical Pharmacology*, 32:529-531, (1987).

Thysman, "Anesthesia & Analgesia", vol. 77 No. 1 Jul. 1993, (Jul. 1, 1993), 61-66.

Thysman, Sophie, "In Vivo Iontophoresis of Fentanyl and Sufentanil in Rats: Pharmacokinetics and Acute Antionociceptive Effects", *Anesthesia & Analgesia*, vol. 77, No. 1, XP000576408, (1993), 61-66.

Thysman, Sophie, "Transdermal Iontopheresis of Fentanyl: Delivery and Mechanistic Analysis", *International Journal of Pharmaceutics 101*, Elsevier Science Publishers B.V., (1994), 105-113.

* cited by examiner

DEVICE FOR TRANSDERMAL ELECTROTRANSPORT DELIVERY OF FENTANYL AND SUFENTANIL

CROSS-REFERENCE TO RELATED APPLICATIONS

This is a continuation of U.S. patent application Ser. No. 11/260,976, filed Oct. 28, 2005, which is a continuation of U.S. patent application Ser. No. 10/190,022, filed Jul. 2, 2002, now U.S. Pat. No. 7,018,370, which is a continuation of U.S. patent application Ser. No. 09/781,041, filed Feb. 9, 2001, now U.S. Pat. No. 6,425,892, which is a continuation of U.S. patent application Ser. No. 08/952,657 filed Mar. 17, 1998, now U.S. Pat. No. 6,216,033, which is a §371 of application Ser. No. PCT/US 96/07380, filed May 22, 1996, which is a continuation-in-part of U.S. patent application Ser. No. 08/460,785, filed Jun. 5, 1995, now abandoned, the disclosures of which are specifically incorporated by reference herein in their entireties.

FIELD OF THE INVENTION

The invention relates generally to improved electrotransport drug delivery. Specifically, the invention relates to a device, composition and method for improved electrotransport delivery of analgesic drugs, particularly fentanyl and analogs of fentanyl. A composition is provided in the form of a hydrogel formulation for use in an electrotransport device.

BACKGROUND OF THE INVENTION

The transdermal delivery of drugs, by diffusion through the epidermis, offers improvements over more traditional delivery methods, such as subcutaneous injections and oral delivery. Transdermal drug delivery avoids the hepatic first pass effect encountered with oral drug delivery. Transdermal drug delivery also eliminates patient discomfort associated with subcutaneous injections. In addition, transdermal delivery can provide more uniform concentrations of drug in the bloodstream of the patient over time due to the extended controlled delivery profiles of certain types of transdermal delivery devices. The term "transdermal" delivery, broadly encompasses the delivery of an agent through a body surface, such as the skin, mucosa, or nails of an animal.

The skin functions as the primary barrier to the transdermal penetration of materials into the body and represents the body's major resistance to the transdermal delivery of therapeutic agents such as drugs. To date, efforts have been focused on reducing the physical resistance or enhancing the permeability of the skin for the delivery of drugs by passive diffusion. Various methods for increasing the rate of transdermal drug flux have been attempted, most notably using chemical flux enhancers.

Other approaches to increase the rates of transdermal drug delivery include use of alternative energy sources such as electrical energy and ultrasonic energy. Electrically assisted transdermal delivery is also referred to as electrotransport. The term "electrotransport" as used herein refers generally to the delivery of an agent (e.g., a drug) through a membrane, such as skin, mucous membrane, or nails. The delivery is induced or aided by application of an electrical potential. For example, a beneficial therapeutic agent may be introduced into the systemic circulation of a human body by electrotransport delivery through the skin. A widely used electrotransport process, electromigration (also called iontophoresis), involves the electrically induced transport of charged ions. Another type of electrotransport, electroosmosis, involves the flow of a liquid, which liquid contains the agent to be delivered, under the influence of an electric field. Still another type of electrotransport process, electroporation, involves the formation of transiently-existing pores in a biological membrane by the application of an electric field. An agent can be delivered through the pores either passively (i.e., without electrical assistance) or actively (i.e., under the influence of an electric potential). However, in any given electrotransport process, more than one of these processes, including at least some "passive" diffusion, may be occurring simultaneously to a certain extent. Accordingly, the term "electrotransport", as used herein, should be given its broadest possible interpretation so that it includes the electrically induced or enhanced transport of at least one agent, which may be charged, uncharged, or a mixture thereof, whatever the specific mechanism or mechanisms by which the agent actually is transported.

Electrotransport devices use at least two electrodes that are in electrical contact with some portion of the skin, nails, mucous membrane, or other surface of the body. One electrode, commonly called the "donor" electrode, is the electrode from which the agent is delivered into the body. The other electrode, typically termed the "counter" electrode, serves to close the electrical circuit through the body. For example, if the agent to be delivered is positively charged, i.e., a cation, then the anode is the donor electrode, while the cathode is the counter electrode which serves to complete the circuit. Alternatively, if an agent is negatively charged, i.e., an anion, the cathode is the donor electrode and the anode is the counter electrode. Additionally, both the anode and cathode may be considered donor electrodes if both anionic and cationic agent ions, or if uncharged dissolved agents, are to be delivered.

Furthermore, electrotransport delivery systems generally require at least one reservoir or source of the agent to be delivered to the body. Examples of such donor reservoirs include a pouch or cavity, a porous sponge or pad, and a hydrophilic polymer or a gel matrix. Such donor reservoirs are electrically connected to, and positioned between, the anode or cathode and the body surface, to provide a fixed or renewable source of one or more agents or drugs. Electrotransport devices also have an electrical power source such as one or more batteries. Typically at any one time, one pole of the power source is electrically connected to the donor electrode, while the opposite pole is electrically connected to the counter electrode. Since it has been shown that the rate of electrotransport drug delivery is approximately proportional to the electric current applied by the device, many electrotransport devices typically have an electrical controller that controls the voltage and/or current applied through the electrodes, thereby regulating the rate of drug delivery. These control circuits use a variety of electrical components to control the amplitude, polarity, timing, waveform shape, etc. of the electric current and/or voltage supplied by the power source. See, for example, McNichols et al., U.S. Pat. No. 5,047,007.

To date, commercial transdermal electrotransport drug delivery devices (e.g., the Phoresor, sold by Iomed, Inc. of Salt Lake City, Utah; the Dupel Iontophoresis System sold by Empi, Inc. of St. Paul, Minn.; the Webster Sweat Inducer, model 3600, sold by Wescor, Inc. of Logan, Utah) have generally utilized a desk-top electrical power supply unit and a pair of skin contacting electrodes. The donor electrode contains a drug solution while the counter electrode contains a solution of a biocompatible electrolyte salt. The power supply unit has electrical controls for adjusting the amount of electrical current applied through the electrodes. The "satellite" electrodes are connected to the electrical power supply unit by long (e.g., 1-2 meters) electrically conductive wires or cables. The wire connections are subject to disconnection and limit the patient's movement and mobility. Wires between electrodes and controls may also be annoying or uncomfortable to the patient. Other examples of desk-top electrical power supply units which use "satellite" electrode assemblies are disclosed in Jacobsen et al., U.S. Pat. No. 4,141,359 (see FIGS. 3 and 4); LaPrade, U.S. Pat. No. 5,006,108 (see FIG. 9); and Maurer et al., U.S. Pat. No. 5,254,081.

More recently, small self-contained electrotransport delivery devices have been proposed to be worn on the skin, sometimes unobtrusively under clothing, for extended periods of time. Such small self-contained electrotransport delivery devices are disclosed for example in Tapper, U.S. Pat. No. 5,224,927; Sibalis, et al., U.S. Pat. No. 5,224,928; and Haynes et al., U.S. Pat. No. 5,246,418.

There have recently been suggestions to utilize electrotransport devices having a reusable controller which is adapted for use with multiple drug-containing units. The drug-containing units are simply disconnected from the controller when the drug becomes depleted and a fresh drug-containing unit is thereafter connected to the controller. In this way, the relatively more expensive hardware components of the device (e.g. batteries, LED's, circuit hardware, etc.) can be contained within the reusable controller, and the relatively less expensive donor reservoir and counter reservoir matrices can be contained in the single use/disposable drug-containing unit, thereby bringing down the overall cost of electrotransport drug delivery. Examples of electrotransport devices comprised of a reusable controller, removably connected to a drug-containing unit are disclosed in Sage, Jr. et al., U.S. Pat. No. 5,320,597; Sibalis, U.S. Pat. No. 5,358,483; Sibalis et al., U.S. Pat. No. 5,135,479 (FIG. 12); and Devane et al., UK Patent Application 2 239 803.

In further development of electrotransport devices, hydrogels have become particularly favored for use as the drug and electrolyte reservoir matrices, in part, due to the fact that water is the preferred liquid solvent for use in electrotransport drug delivery due to its excellent biocompatibility compared with other liquid solvents such as alcohols and glycols. Hydrogels have a high equilibrium water content and can quickly absorb water. In addition, hydrogels tend to have good biocompatibility with the skin and with mucosal membranes.

Of particular interest in transdermal delivery is the delivery of analgesic drugs for the management of moderate to severe pain. Control of the rate and duration of drug delivery is particularly important for transdermal delivery of analgesic drugs to avoid the potential risk of overdose and the discomfort of an insufficient dosage.

One class of analgesics that has found application in a transdermal delivery route is the synthetic opiates, a group of 4-aniline piperidines. The synthetic opiates, e.g., fentanyl and certain of its derivatives such as sufentanil, are particularly well-suited for transdermal administration. These synthetic opiates are characterized by their rapid onset of analgesia, high potency, and short duration of action. They are estimated to be 80 and 800 times respectively, more potent than morphine. These drugs are weak bases, i.e., amines, whose major fraction is cationic in acidic media.

In an in vivo study to determine plasma concentration, Thysman and Preat (Anesth. Analg. 77 (1993) pp. 61-66) compared simple diffusion of fentanyl and sufentanil to electrotransport delivery in citrate buffer at pH 5. Simple diffusion did not produce any detectable plasma concentration. The plasma levels attainable depended on the maximum flux of the drug that can cross the skin and the drug's pharmacokinetic properties, such as clearance and volume of distribution. Electrotransport delivery was reported to have significantly reduced lag time (i.e., time required to achieve peak plasma levels) as compared to passive transdermal patches (1.5 h versus 14 h). The researchers' conclusions were that electrotransport of these analgesic drugs can provide more rapid control of pain than classical patches, and a pulsed release of drug (by controlling electrical current) was comparable to the constant delivery of classical patches. See, also, e.g., Thysman et al. Int. J. Pharma., 101 (1994) pp. 105-113; V. Preat et al. Int. J. Pharma., 96 (1993) pp. 189-196 (sufentanil); Gourlav et al. Pain, 37 (1989) pp. 193-202 (fentanyl); Sebel et al. Eur. J. Clin. Pharmacol., 32 (1987) pp. 529-531 (fentanyl and sufentanil). Passive, i.e., by diffusion, and electrically-assisted transdermal delivery of narcotic analgesic drugs, such as fentanyl, to induce analgesia, have also both been described in the patent literature. See, for example, Gale et al., U.S. Pat. No. 4,588,580, and Theeuwes et al., U.S. Pat. No. 5,232,438.

In the last several years, management of post-operative pain has looked to delivery systems other than electrotransport delivery. Particular attention has been given to devices and systems which permit, within predetermined limits, the patient to control the amount of analgesic the patient receives. The experience with these types of devices has generally been that patient control of the administration of analgesic has resulted in the administration of less analgesic to the patient than would have been administered were the dosage prescribed by a physician. Self-administered or patient controlled self-administration has become known (and will be referred to herein) as patient-controlled analgesia (PCA).

Known PCA devices are typically electromechanical pumps which require large capacity electrical power sources, e.g., alternating current or multiple large capacity battery packs which are bulky. Due to their bulk and complexity, commercially available PCA devices generally require the patient to be confined to a bed, or some other essentially fixed location. Known PCA devices deliver drug to the patient by means of an intravenous line or a catheter which must be inserted into the intended vein, artery or other organ by a qualified medical technician. This technique requires that the skin barrier be breached in order to administer the analgesic. (See, Zdeb U.S. Pat. No. 5,232,448). Thus, as practiced using commercially available PCA devices, PCA requires the presence of highly skilled medical technicians to initiate and supervise the operation of the PCA device along with its attendant risk of infection. Further, commercially available PCA devices themselves are somewhat painful to use by virtue of their percutaneous (i.e., intravenous or subcutaneous) access.

The art has produced little in the way of transdermal electrotransport devices that can compete with the conventional PCAs in terms of the amount of drug delivered to achieve adequate analgesia and in a patient controlled manner. Further, little progress has been made to provide a hydrogel formulation for analgesic electrotransport, particularly fentanyl transdermal electrotransport delivery, that has long term stability and has performance characteristics comparable to the patient controlled electromechanical pumps for, e.g., intravenous delivery of analgesic. There is need to provide an analgesic formulation in a suitable device to take advantage of the convenience of electrotransport delivery in a small, self-contained, patient-controlled device.

SUMMARY OF THE INVENTION

The present invention provides a device for improved transdermal electrotransport delivery of fentanyl and analogs of fentanyl, particularly sufentanil. As such, the device of the present invention provides a greater degree of efficiency in electrotransport delivery of analgesic fentanyl or sufentanil, concomitantly providing a greater measure of patient safety and comfort in pain management. The foregoing, and other advantages of the present invention, are provided by a device for delivering fentanyl or sufentanil through a body surface (e.g., intact skin) by electrotransport, the device having a anodic donor reservoir containing an at least partially aqueous solution of a fentanyl/sufentanil salt.

The present invention concerns a device for administering fentanyl or sufentanil by transdermal electrotransport in order to treat moderate-to-severe pain associated with major surgical procedures. A transdermal electrotransport dose of about 20 μg to about 60 μg of fentanyl, delivered over a delivery interval of up to about 20 minutes, is therapeutically effective in treating moderate-to-severe post-operative pain in human patients having body weights above about 35 kg. Preferably, the amount of fentanyl delivered is about 35 μg to about 45 μg over a delivery interval of about 5 to 15 minutes, and most preferably the amount of fentanyl delivered is about 40 μg over a delivery interval of about 10 minutes. Since fentanyl has a relatively short distribution half-life once delivered into a human body (i.e., about 3 hours), the device for inducing analgesia preferably includes means for maintaining the analgesia so induced. Thus, the device for transdermally delivering fentanyl by electrotransport preferably includes means for delivering at least 1 additional, more preferably about 10 to 100 additional, and most preferably about 20 to 80 additional, like dose(s) of fentanyl over subsequent like delivery interval(s) over a 24 hour period. The ability to deliver multiple identical doses from a transdermal electrotransport fentanyl delivery device also provides the capability of pain management to a wider patient population, in which different patients require different amounts of fentanyl to control their pain. By providing the capability of administering multiple small transdermal electrotransport fentanyl doses, the patients can titrate themselves to administer only that amount of fentanyl which is needed to control their pain, and no more.

Other advantages and a fuller appreciation of specific adaptations, compositional variations, and physical attributes of the present invention can be learned from an examination of the following drawings, detailed description, examples, and appended claims.

BRIEF DESCRIPTION OF THE DRAWINGS

The present invention is hereinafter described in conjunction with the appended drawings, in which.

DETAILED DESCRIPTION OF THE INVENTION

Figure 1:
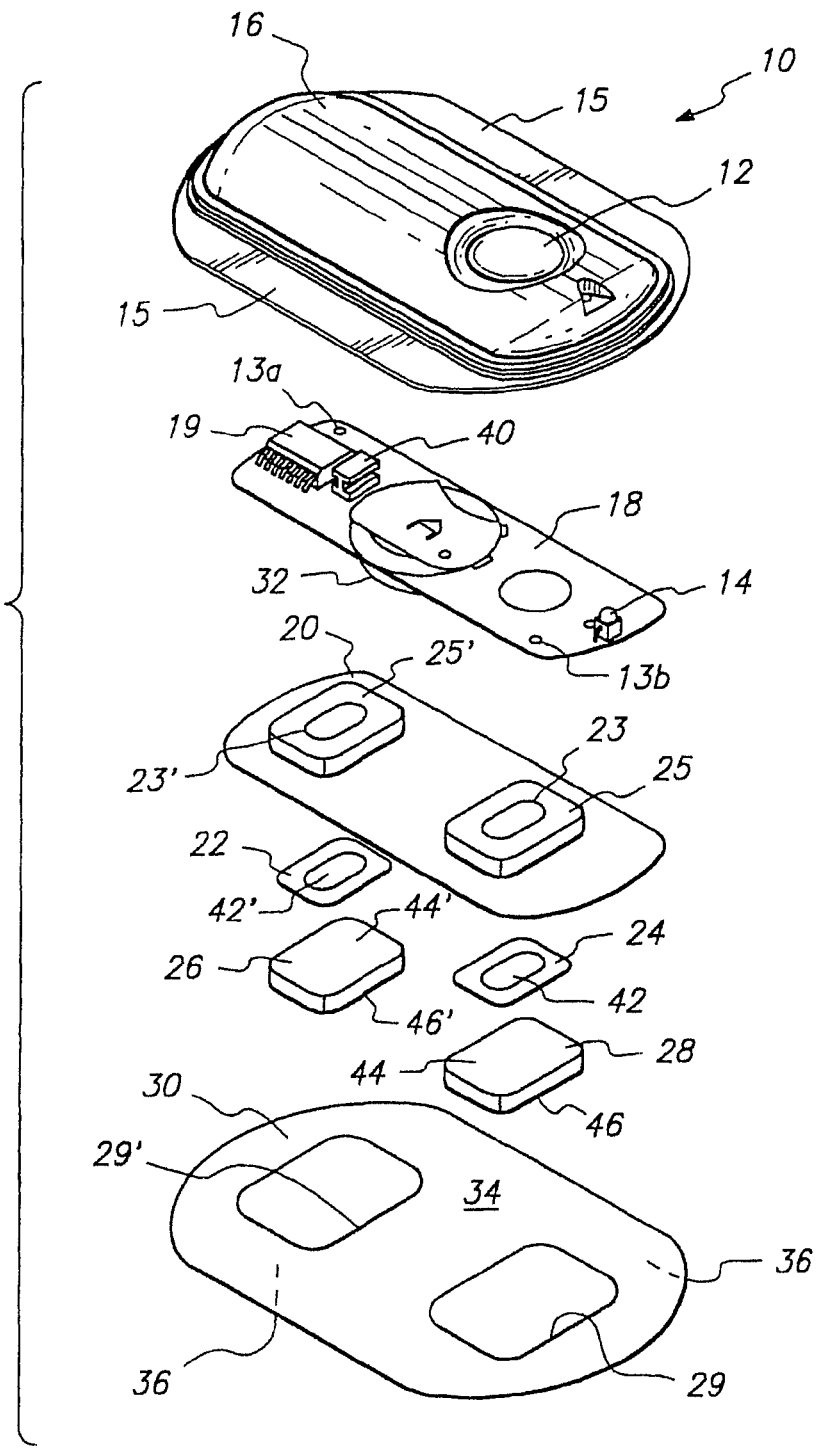
FIG. 1 is a perspective exploded view of an electrotransport drug delivery device in accordance with the present invention.

The present invention provides a fentanyl or sufentanil salt electrotransport delivery device, and a method of using same, to achieve a systemic analgesic effect which is comparable to the effect achieved in known IV accessed patient controlled analgesic pumps. The present invention provides an electrotransport delivery device for delivering fentanyl or sufentanil through a body surface, e.g., skin, to achieve the analgesic effect. The fentanyl or sufentanil salt is provided in a donor reservoir of an electrotransport delivery device, preferably as an aqueous salt solution.

The dose of fentanyl delivered by transdermal electrotransport is about 20 μg to about 60 μg over a delivery time of up to about 20 minutes in human patients having body weights of 35 kg or greater. Preferred is a dosage of about 35 μg to about 45 μg, and most preferred is a dosage of about 40 μg for the delivery period. The device of the invention further preferably includes means for delivering about 10 to 100, and more preferably about 20 to 80 additional like doses over a period of 24 hours in order to achieve and maintain the analgesic effect.

The dose of sufentanil delivered by transdermal electrotransport is about 2.3 μg to about 7.0 μg over a delivery time of up to about 20 minutes in human patients having a body weights of 35 kg or greater. Preferred is a dosage of about 4 μg to about 5.5 μg, and most preferred is a dosage of about 4.7 μg for the delivery period. The device of the invention further preferably includes means for delivering about 10 to 100, and more preferably about 20 to 80 additional like doses over a period of 24 hours in order to achieve and maintain the analgesic effect.

The fentanyl/sufentanil salt-containing anodic reservoir formulation for transdermally delivering the above mentioned doses of fentanyl/sufentanil by electrotransport is preferably comprised of an aqueous solution of a water soluble fentanyl/sufentanil salt such as HCl or citrate salts. Most preferably, the aqueous solution is contained within a hydrophilic polymer matrix such as a hydrogel matrix. The fentanyl/sufentanil salt is present in an amount sufficient to deliver the above mentioned doses transdermally by electrotransport over a delivery period of up to about 20 minutes, to achieve a systemic analgesic effect. The fentanyl/sufentanil salt typically comprises about 1 to 10 wt % of the donor reservoir formulation (including the weight of the polymeric matrix) on a fully hydrated basis, and more preferably about 1 to 5 wt % of the donor reservoir formulation on a fully hydrated basis. Although not critical to this aspect of the present invention, the applied electrotransport current density is typically in the range of about 50 to 150 μA/cm2 and the applied electrotransport current is typically in the range of about 150 to 240 μA.

The anodic fentanyl/sufentanil salt-containing hydrogel can suitably be made of any number of materials but preferably is comprised of a hydrophilic polymeric material, preferably one that is polar in nature so as to enhance the drug stability. Suitable polar polymers for the hydrogel matrix comprise a variety of synthetic and naturally occurring polymeric materials. A preferred hydrogel formulation contains a suitable hydrophilic polymer, a buffer, a humectant, a thickener, water and a water soluble fentanyl or sufentanil salt (e.g., HCl salt). A preferred hydrophilic polymer matrix is polyvinyl alcohol such as a washed and fully hydrolyzed polyvinyl alcohol (PVOH), e.g., Mowiol 66-100 commercially available from Hoechst Aktiengesellschaft. A suitable buffer is an ion exchange resin which is a copolymer of methacrylic acid and divinylbenzene in both an acid and salt form. One example of such a buffer is a mixture of Polacrilin (the copolymer of methacrylic acid and divinyl benzene available from Rohm & Haas, Philadelphia, Pa.) and the potassium salt thereof. A mixture of the acid and potassium salt forms of Polacrilin functions as a polymeric buffer to adjust the pH of the hydrogel to about pH 6. Use of a humectant in the hydrogel formulation is beneficial to inhibit the loss of moisture from the hydrogel. An example of a suitable humectant is guar gum. Thickeners are also beneficial in a hydrogel formulation. For example, a polyvinyl alcohol thickener such as hydroxypropyl methylcellulose (e.g., Methocel K100 MP available from Dow Chemical, Midland, Mich.) aids in modifying the rheology of a hot polymer solution as it is dispensed into a mold or cavity. The hydroxypropyl methylcellulose increases in viscosity on cooling and significantly reduces the propensity of a cooled polymer solution to overfill the mold or cavity.

In one preferred embodiment, the anodic fentanyl/sufentanil salt-containing hydrogel formulation comprises about 10 to 15 wt % polyvinyl alcohol, 0.1 to 0.4 wt % resin buffer, and about 1 to 2 wt % fentanyl or sufentanil salt, preferably the hydrochloride salt. The remainder is water and ingredients such as humectants, thickeners, etc. The polyvinyl alcohol (PVOH)-based hydrogel formulation is prepared by mixing all materials, including the fentanyl or sufentanil salt, in a single vessel at elevated temperatures of about 90° C. to 95° C. for at least about 0.5 hr. The hot mix is then poured into foam molds and stored at freezing temperature of about −35° C. overnight to cross-link the PVOH. Upon warming to ambient temperature, a tough elastomeric gel is obtained suitable for fentanyl electrotransport.

The hydrogel formulations are used in an electrotransport device such as described hereinafter. A suitable electrotransport device includes an anodic donor electrode, preferably comprised of silver, and a cathodic counter electrode, preferably comprised of silver chloride. The donor electrode is in electrical contact with the donor reservoir containing the aqueous solution of a fentanyl/sufentanil salt. As described above, the donor reservoir is preferably a hydrogel formulation. The counter reservoir also preferably comprises a hydrogel formulation containing a (e.g., aqueous) solution of a biocompatible electrolyte, such as citrate buffered saline. The anodic and cathodic hydrogel reservoirs preferably each have a skin contact area of about 1 to 5 cm2 and more preferably about 2 to 3 cm2. The anodic and cathodic hydrogel reservoirs preferably have a thickness of about 0.05 to 0.25 cm, and more preferably about 0.15 cm. The applied electrotransport current is about 150 µA to about 240 µA, depending on the analgesic effect desired. Most preferably, the applied electrotransport current is substantially constant DC current during the dosing interval.

Reference is now made to FIG. 1 which depicts an exemplary electrotransport device which can be used in accordance with the present invention. FIG. 1 shows a perspective exploded view of an electrotransport device 10 having an activation switch in the form of a push button switch 12 and a display in the form of a light emitting diode (LED) 14. Device 10 comprises an upper housing 16, a circuit board assembly 18, a lower housing 20, anode electrode 22, cathode electrode 24, anode reservoir 26, cathode reservoir 28 and skin-compatible adhesive 30. Upper housing 16 has lateral wings 15 which assist in holding device 10 on a patient's skin. Upper housing 16 is preferably composed of an injection moldable elastomer (e.g., ethylene vinyl acetate). Printed circuit board assembly 18 comprises an integrated circuit 19 coupled to discrete electrical components 40 and battery 32. Circuit board assembly 18 is attached to housing 16 by posts (not shown in FIG. 1) passing through openings 13a and 13b, the ends of the posts being heated/melted in order to heat stake the circuit board assembly 18 to the housing 16. Lower housing 20 is attached to the upper housing 16 by means of adhesive 30, the upper surface 34 of adhesive 30 being adhered to both lower housing 20 and upper housing 16 including the bottom surfaces of wings 15.

Shown (partially) on the underside of circuit board assembly 18 is a battery 32, which is preferably a button cell battery and most preferably a lithium cell. Other types of batteries may also be employed to power device 10.

The circuit outputs (not shown in FIG. 1) of the circuit board assembly 18 make electrical contact with the electrodes 24 and 22 through openings 23,23' in the depressions 25,25' formed in lower housing, by means of electrically conductive adhesive strips 42,42'. Electrodes 22 and 24, in turn, are in direct mechanical and electrical contact with the top sides 44', 44 of reservoirs 26 and 28. The bottom sides 46', 46 of reservoirs 26,28 contact the patient's skin through the openings 29',29 in adhesive 30. Upon depression of push button switch 12, the electronic circuitry on circuit board assembly 18 delivers a predetermined DC current to the electrodes/reservoirs 22,26 and 24,28 for a delivery interval of predetermined length, e.g., about 10 minutes. Preferably, the device transmits to the user a visual and/or audible confirmation of the onset of the drug delivery, or bolus, interval by means of LED 14 becoming lit and/or an audible sound signal from, e.g., a "beeper". Analgesic drug, e.g. fentanyl, is then delivered through the patient's skin, e.g., on the arm, for the predetermined (e.g., 10 minute) delivery interval. In practice, a user receives feedback as to the onset of the drug delivery interval by visual (LED 14 becomes lit) and/or audible signals (a beep from the "beeper").

Anodic electrode 22 is preferably comprised of silver and cathodic electrode 24 is preferably comprised of silver chloride. Both reservoirs 26 and 28 are preferably comprised of polymer hydrogel materials as described herein. Electrodes 22, 24 and reservoirs 26, 28 are retained by lower housing 20. For fentanyl and sufentanil salts, the anodic reservoir 26 is the "donor" reservoir which contains the drug and the cathodic reservoir 28 contains a biocompatible electrolyte.

The push button switch 12, the electronic circuitry on circuit board assembly 18 and the battery 32 are adhesively "sealed" between upper housing 16 and lower housing 20. Upper housing 16 is preferably composed of rubber or other elastomeric material. Lower housing 20 is preferably composed of a plastic or elastomeric sheet material (e.g., polyethylene) which can be easily molded to form depressions 25,25' and cut to form openings 23,23'. The assembled device 10 is preferably water resistant (i.e., splash proof and is most preferably waterproof. The system has a low profile that easily conforms to the body thereby allowing freedom of movement at, and around, the wearing site. The anode/drug reservoir 26 and the cathode/salt reservoir 28 are located on the skin-contacting side of device 10 and are sufficiently separated to prevent accidental electrical shorting during normal handling and use.

The device 10 adheres to the patient's body surface (e.g., skin) by means of a peripheral adhesive 30 which has upper side 34 and body-contacting side 36. The adhesive side 36 has adhesive properties which assures that the device 10 remains in place on the body during normal user activity, and yet permits reasonable removal after the predetermined (e.g., 24-hour) wear period. Upper adhesive side 34 adheres to lower housing 20 and retains the electrodes and drug reservoirs within housing depressions 25, 25' as well as retains lower housing 20 attached to upper housing 16.

The push button switch 12 is located on the top side of device 10 and is easily actuated through clothing. A double press of the push button switch 12 within a short period of time, e.g., three seconds, is preferably used to activate the device 10 for delivery of drug, thereby minimizing the likelihood of inadvertent actuation of the device 10.

Upon switch activation an audible alarm signals the start of drug delivery, at which time the circuit supplies a predetermined level of DC current to the electrodes/reservoirs for a predetermined (e.g., 10 minute) delivery interval. The LED 14 remains "on" throughout the delivery interval indicating that the device 10 is in an active drug delivery mode. The battery preferably has sufficient capacity to continuously power the device 10 at the predetermined level of DC current for the entire (e.g., 24 hour) wearing period.

Preferably, the concentration of fentanyl or sufentanil in solution in the donor reservoir is maintained at or above the level at which the transdermal electrotransport fentanyl/sufentanil flux is independent of drug concentration in the donor reservoir during the electrotransport drug delivery period. Transdermal electrotransport fentanyl flux begins to become dependent upon the concentration of the fentanyl salt in aqueous solution as the fentanyl salt concentration falls below about 11 to 16 mM. The 11 to 16 mM concentration is calculated based only on the volume of liquid solvent used in the donor reservoir, not on the total volume of the reservoir. In other words, the 11 to 16 mM concentration does not include the volume of the reservoir which is represented by the reservoir matrix (e.g., hydrogel or other matrix) material. Furthermore, the 11 to 16 mM concentration is based upon the number of moles of fentanyl salt, not the equivalent number of moles of fentanyl free base, which is contained in the donor reservoir solution. For fentanyl HCl, the 11 to 16 mM concentration is equivalent to about 4 to 6 mg/mL. Other fentanyl salts (e.g., fentanyl citrate) will have slightly differing weight based concentration ranges based on the difference in the molecular weight of the counter ion of the particular fentanyl salt in question. As the fentanyl salt concentration falls to about 11 to 16 mM, the fentanyl transdermal electrotransport flux begins to significantly decline, even if the applied electrotransport current remains constant. Thus, to ensure a predictable fentanyl flux with a particular level of applied electrotransport current, the fentanyl salt concentration in the solution contained in the donor reservoir is preferably maintained above about 11 mM, and more preferably above about 16 mM. In addition to fentanyl, water soluble salts of sufentanil also have minimum aqueous solution concentrations below which the transdermal electrotransport flux becomes dependent on concentration of the sufentanil salt in solution. The minimum concentration for sufentanil is about 1.7 mM, which for sufentanil citrate is equivalent to about 1 mg/mL.

Since fentanyl and sufentanil are both bases, the salts of fentanyl and sufentanil are typically acid addition salts, e.g., citrate salts, hydrochloride salts, etc. The acid-addition-salts of fentanyl typically have water solubilities of about 25 to 30 mg/mL. The acid addition salts of sufentanil typically have water solubilities of about 45 to 50 mg/mL. When these salts are placed in solution (e.g., aqueous solution), the salts dissolve and form protonated fentanyl or sufentanil cations and counter (e.g., citrate or chloride) anions. As such, the fentanyl/sufentanil cations are delivered from the anodic electrode of an electrotransport delivery device. Silver anodic electrodes have been proposed for transdermal electrotransport delivery as a way to maintain pH stability in the anodic reservoir. See for example, Untereker et al U.S. Pat. No. 5,135,477 and Petelenz et al U.S. Pat. No. 4,752,285. These patents also recognize one of the shortcomings of using a silver anodic electrode in an electrotransport delivery device, namely that the application of current through the silver anode causes the silver to become oxidized ($Ag \rightarrow Ag^+ + e^-$) thereby forming silver cations which compete with the cationic drug for delivery into the skin by electrotransport. Silver ion migration into the skin results in a transient epidermal discoloration (TED) of the skin. In accordance with the teachings in these patents, the cationic fentanyl and sufentanil are preferably formulated as a halide salt (e.g., hydrochloride salt) so that any electrochemically-generated silver ions will react with the drug counter ions (i.e., halide ions) to form a substantially insoluble silver halide ($Ag^+ + X^- \rightarrow AgX$). In addition to these patents, Phipps et al, WO 95/27530 teaches the use of supplementary chloride ion sources in the form of high molecular weight chloride resins in the donor reservoir of a transdermal electrotransport delivery device. These resins are highly effective at providing sufficient chloride for preventing silver ion migration, and the attendant skin discoloration when delivering fentanyl or sufentanil transdermally by electrotransort using a silver anodic electrode.

The present invention is further explained by the following examples which illustrative of, but do not limit the scope of, the present invention.

EXAMPLES

Example 1

The following studies were conducted to determine the transdermal electrotransport dosing level required to achieve an acceptable level of analgesia in human patients suffering from moderate to severe post-operative pain. The study was conducted in 132 post-operative male and female patients who were expected to have moderate to severe pain after surgery, including orthopedic (shoulder, knee, long bone) and abdominal (urological, gynecological) surgeries. The patients wore one of two different electrotransport fentanyl HCl delivery devices on the upper arm for 24 hours following surgery. Both devices applied electrotransport current for a delivery interval of 10 minutes upon activating a push button switch on the device. The first device, worn by 79 of the 132 patients, applied an electrotransport current of 150 µA which delivered an average fentanyl dose of 25 µg over the 10 minute delivery interval. The second device, worn by 53 of the 132 patients, applied an electrotransport current of 240 µA which delivered an average fentanyl dose of 40 µg over the 10 minute delivery interval.

In both devices, the patients could self-administer up to 6 doses every hour. Patients using the first (i.e., 25 µg dose) device could apply a maximum of 144 doses. Patients using the second (i.e., 40 µg dose) device were allowed to apply up to a maximum number of 80 doses.

Both devices were two-part systems which included a reusable electronic controller and a single use/disposable drug-containing unit. Each drug unit contained an anodic fentanyl HCl-containing donor gel and a cathodic saline-containing counter gel. All gels had a skin contact area of 2 $cm^2$ and a thickness of 0.16 cm. The approximate weight of the donor gels was 350 mg. The anodic donor gels in the 25 µg dose and 40 µg dose systems were the same size and composition, only the applied electrotransport current level was different. The cathodic counter electrode assemblies each had a PVOH based gel which contained citrate buffered saline. A silver chloride cathodic electrode was laminated to one surface of the counter gel. The 25 µg and µg dose anodic gels had the following composition:

| Material | (wt %) |
|---|---|
| Water | 73.2 |
| PVOH | 10.0 |

-continued

| Material | (wt %) |
|---|---|
| Fentanyl HCl | 1.4 |
| Polacrilin | 0.3 |
| Polacrilin potassium | 0.1 |
| Glycerin | 5.0 |
| Cholestyramine resin | 10.0 |

All patients were initially titrated to an acceptable level of analgesia with intravenous (IV) fentanyl in the recovery room immediately following surgery. Within 3 hours after surgery when the patients had met the usual institutional standards for discharge from the recovery room and were able to operate their worn electrotransport delivery device, the patients were moved to a ward where they could self administer fentanyl by transdermal electrotransport for the management of their pain. In the event the electrotransport fentanyl delivery regimen was insufficient to control pain, the patients were retitrated with supplemental fentanyl through IV administration to achieve adequate analgesia.

In the 25 µg dose group, 38 of 79 patients (i.e., 48%) required no supplemental IV fentanyl after leaving the recovery room. In the 40 µg dose group, 47 of 53 patients (i.e., 89%) required no supplemental IV fentanyl after leaving the recovery room. Based on these percentages, it was determined that the 25 µg dose regimen was sufficient to treat the pain associated with these types of surgical procedures in about one-half of the patients; and the 40 µg dose regimen was sufficient to treat the pain associated with these types of surgical procedures in about 90% of the patients tested. Because the 25 µg dose regimen was analgesically effective for about half the patients, lower dosing regimens of about 20 to 30 µg and preferably about 20 to 25 pg of fentanyl over these same dosing intervals (i.e., up to 20 minutes) are also effective, and less susceptible to unintentional over-dosing, in treating less severe acute pain such as that experienced with hernia repair, kidney stones, arthritis pain, laparoscopic procedures, and other conditions involving less severe pain than that associated with major surgeries. The corresponding lower dosing regimens for sufentanil are about 2.3 µg to about 3.5 µg, and preferably about 2.3 µg to about 2.9 µg, delivered over these same dosing intervals (i.e., up to 20 minutes).

Pain intensity was assessed at baseline immediately before activation of the first on-demand dose and again at times 0.5, 1, 2, 3, 4, 6, 8, 12, 16, 20 and 24 hours after the devices were first activated. The patients were asked to assess pain intenisty by marking on a 10 cm long strip, containing a scale of 1 to 100, with 1 being associated with no pain and 100 being associated with the most severe intensity pain. The quality of analgesia was evaluated by a categorical rating of excellent, good, fair or unsatisfactory according to the same time schedule as that for the pain intensity measurements.

Figure 2:
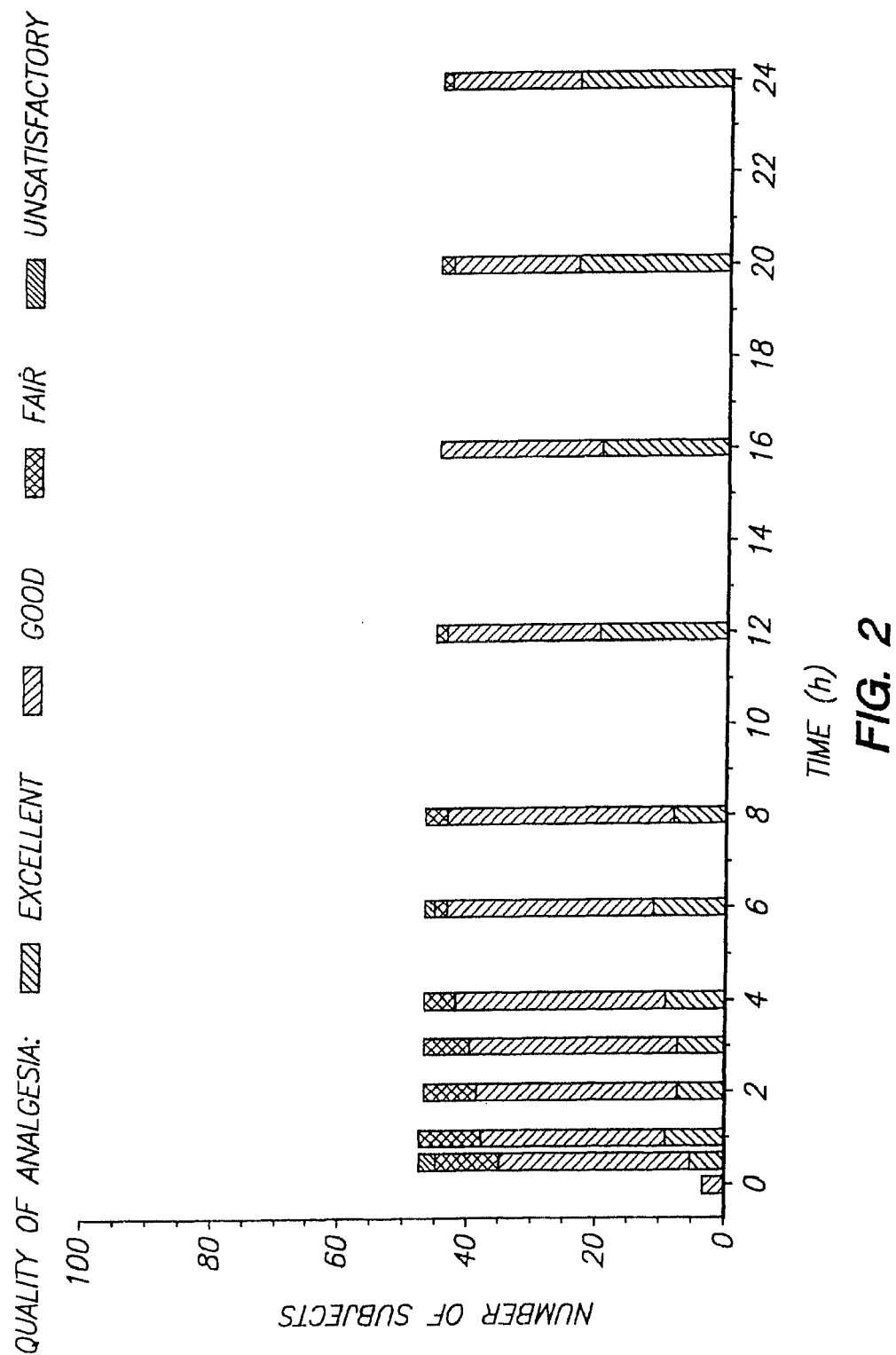
FIG. 2 is a graph illustrating quality of analgesia in patients administered with transdermal electrotransport fentanyl as a function of time.
Figure 3:
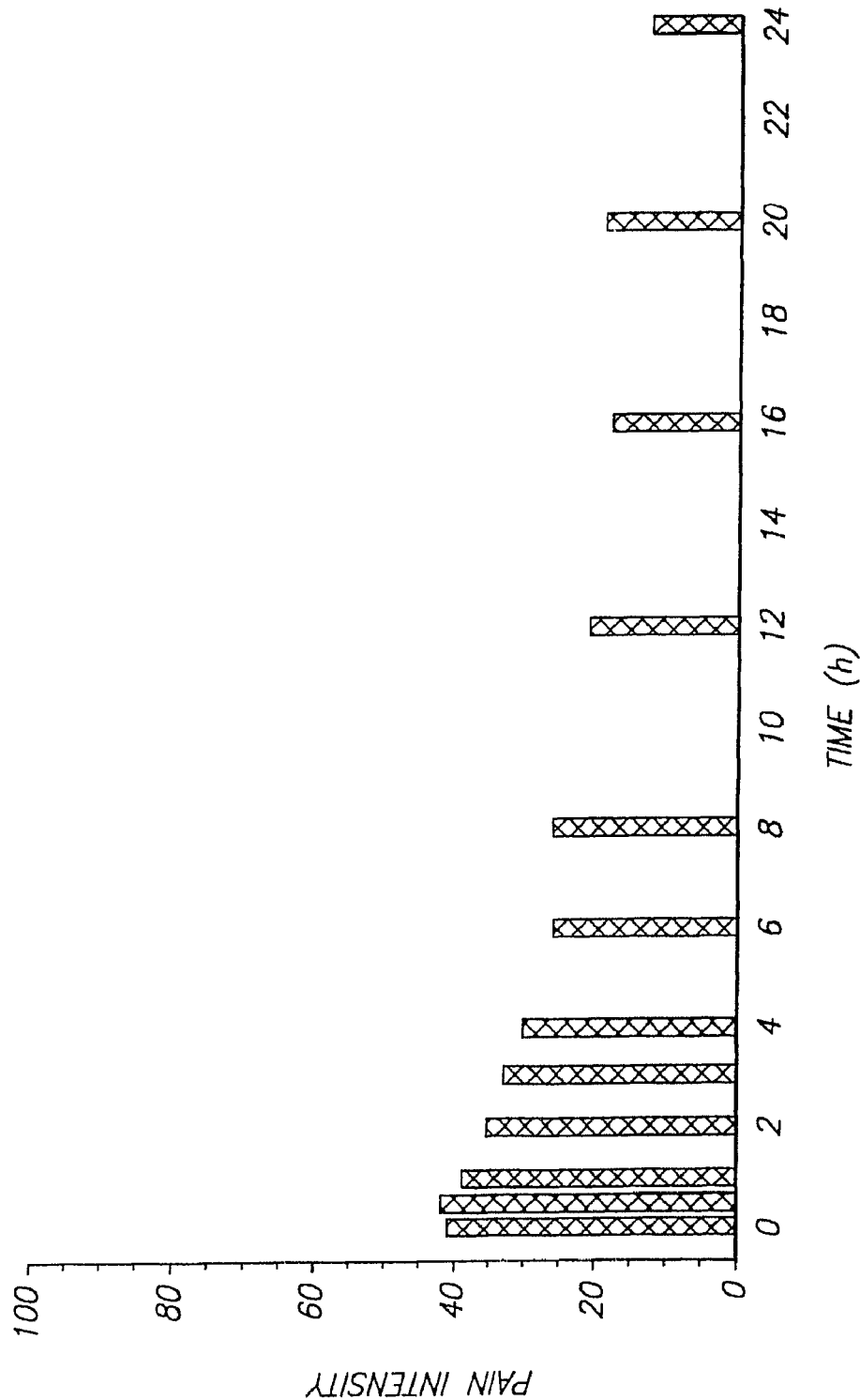
FIG. 3 is a graph illustrating pain intensity experienced by patients administered transdermal electrotransport fentanyl as a function of time.

The quality of analgesia and pain intensity data for the 53 patients using the 40 µg dose electrotransport devices are shown in FIGS. 2 and 3, respectively.

Skin sites beneath the anode and cathode gels were assessed at 1, 6 and 24 hours following removal of the devices and evaluated for topical (e.g., irritation) effects. The topical effects data are shown in Table 1.

TABLE 1

| Hours Post Removal | ETS Skin Site | Score | Edema (%) | Erythema (%) | Extent of Erythema (%) | Itching (%) | Papules (%) | Pustules (%) |
|---|---|---|---|---|---|---|---|---|
| 1 | Anode | 0 | 74 | 15 | 19 | 91 | 92 | 100 |
|   |       | 1 | 8  | 49 | 32 | 6  | 6  | 0 |
|   |       | 2 | 19 | 36 | 49 | 4  | 2  | 0 |
|   | Cathode | 0 | 92 | 72 | 74 | 94 | 94 | 100 |
|   |       | 1 | 6  | 19 | 13 | 4  | 6  | 0 |
|   |       | 2 | 2  | 9  | 13 | 2  | 0  | 0 |
| 6 | Anode | 0 | 74 | 15 | 17 | 89 | 92 | 100 |
|   |       | 1 | 11 | 43 | 34 | 8  | 8  | 0 |
|   |       | 2 | 15 | 40 | 49 | 4  | 0  | 0 |
|   |       | 3 | 0  | 2  | 0  | 0  | 0  | 0 |
|   | Cathode | 0 | 92 | 68 | 68 | 91 | 91 | 100 |
|   |       | 1 | 4  | 19 | 13 | 9  | 6  | 0 |
|   |       | 2 | 4  | 9  | 19 | 0  | 4  | 0 |
|   |       | 3 | 0  | 4  | 0  | 0  | 0  | 0 |
| 24 | Anode | 0 | 83 | 34 | 36 | 91 | 96 | 98 |
|   |       | 1 | 9  | 40 | 38 | 8  | 4  | 2 |
|   |       | 2 | 8  | 26 | 36 | 2  | 0  | 0 |
|   |       | 3 | 0  | 0  | 0  | 0  | 0  | 0 |
|   | Cathode | 0 | 91 | 70 | 70 | 91 | 89 | 98 |
|   |       | 1 | 6  | 19 | 15 | 8  | 8  | 0 |
|   |       | 2 | 4  | 8  | 15 | 2  | 4  | 2 |
|   |       | 3 | 0  | 4  | 0  | 0  | 0  | 0 |

Erythema:
0 = None
1 = Barely perceptible redness
2 = Definite redness
3 = "Beet" redness
Itching:
0 = None
1 = Mild
2 = Moderate
3 = Severe
Edema, Papules, Pustules, Extent of Erythema:
0 = None
1 = <50% of occluded area
2 = >50% of occluded area

Example 2

Two fentanyl hydrochloride-containing anodic donor reservoir PVOH-based gels were made having the following compositions:

| Donor Gel Formulations: | | |
| --- | --- | --- |
| Material | wt % | wt % |
| Purified Water | 86.3 | 85.3 |
| Washed PVOH | 12.0 | 12.0 |
| Fentanyl HCl | 1.7 | 1.7 |
| Hydroxy Methylcellulose | — | 1.0 |

With both formulations, the water and PVOH are mixed at a temperature between 92° C. and 98° C. followed by the addition of fentanyl hydrochloride and subsequent further mixing. The liquid gel was then pumped into foam molds having a disc-shaped cavity. The molds were placed in a freezer overnight at −35° C. to cross-link the PVOH. The gels can be used as anodic donor reservoirs suitable for transdermal electrotransport fentanyl delivery to achieve patient analgesia.

In summary, the present invention provides a device for improving the transdermal electrotransport of water soluble salts of fentanyl and sufentanil. The electrotransport device preferably has a silver anodic donor electrode and a hydrogel based donor reservoir. The electrotransport device is preferably a patient-controlled device. The hydrogel formulation contains a drug concentration which is sufficient to provide an acceptable level of analgesia.

What is claimed is:

1. A patient-worn device for transdermally delivering fentanyl solely by electrically induced or electrically enhanced electrotransport to a human patient suffering from pain, comprising:
    a donor reservoir formulation comprised of a fentanyl salt solution being the sole source of fentanyl in the device;
    a counter reservoir;
    a source of electrical power electrically connected to said reservoirs; and
    a control circuit for controlling electrotransport current, said control circuit including a switch which activates said device and wherein said reservoirs, said power source and said control circuit deliver solely by electrotransport a dose of about 20 µg to about 60 µg of fentanyl over a predetermined delivery period of up to about 20 minutes and terminate said delivery at the end of said delivery period, and wherein said control circuit allows up to 143 additional of said doses over a period of about 24 hours.

2. The device of claim 1, wherein said control circuit allows up to about 10-100 additional of the doses is delivered over a period of about 24 hours.

3. The device of claim 2, wherein said control circuit allows up to about 20-80 additional of the doses is delivered over a period of about 24 hours.

4. A patient-worn device for transdermally delivering sufentanil solely by electrically induced or electrically enhanced electrotransport to a human patient suffering from pain, comprising:
    a donor reservoir formulation comprised of a sufentanil salt solution being the sole source of sufentanil in the device;
    a counter reservoir;
    a source of electrical power electrically connected to said reservoirs; and
    a control circuit for controlling electrotransport current, said control circuit including a switch which activates said device, wherein said donor reservoir, said power source and said control circuit deliver solely by electrotransport a dose of about 2.3 µg to about 7.0 µg of sufentanil over a predetermined delivery period of up to about 20 minutes and terminate said delivery at the end of said delivery period, and wherein said control circuit allows up to 143 additional of said doses over a period of about 24 hours.

5. The device of claim 4, wherein said control circuit allows up to about 10-100 additional of the doses is delivered over a period of about 24 hours.

6. The device of claim 5, wherein said control circuit allows up to about 20-80 additional of the doses is delivered over a period of about 24 hours.

* * * * *